US007955788B2

(12) United States Patent
Zilla et al.

(10) Patent No.: US 7,955,788 B2
(45) Date of Patent: Jun. 7, 2011

(54) BIOPROSTHETIC TISSUE PREPARATION WITH SYNTHETIC HYDROGELS

(75) Inventors: Peter Zilla, Cape Town (ZA); Deon Bezuidenhout, Vredehock (ZA); Anel Oostheysen, Cape Town (ZA); Paul Human, Cape Town (ZA)

(73) Assignee: Medtronic, Inc., Minneapolis, MN (US)

( * ) Notice: Subject to any disclaimer, the term of this patent is extended or adjusted under 35 U.S.C. 154(b) by 1934 days.

(21) Appl. No.: 10/967,365

(22) Filed: Oct. 18, 2004

(65) Prior Publication Data

US 2005/0119736 A1    Jun. 2, 2005

Related U.S. Application Data

(60) Provisional application No. 60/515,618, filed on Oct. 30, 2003.

(51) Int. Cl.
*A01N 1/00* (2006.01)
(52) U.S. Cl. .......................... 435/1.1; 424/423; 623/2.42
(58) Field of Classification Search ................... 435/1.1; 424/423; 623/2.42
See application file for complete search history.

(56) References Cited

U.S. PATENT DOCUMENTS

| | | | | |
|---|---|---|---|---|
| 3,676,406 A * | 7/1972 | Perrino et al. | ................. | 528/337 |
| 4,378,224 A | 3/1983 | Nimni et al. | ................... | 8/94.11 |
| 4,481,009 A | 11/1984 | Nashef | | |
| 4,553,974 A | 11/1985 | Dewanjee | | |
| 4,647,283 A | 3/1987 | Carpentier et al. | ............. | 623/11 |
| 4,648,881 A | 3/1987 | Carpentier et al. | ............. | 623/11 |
| 4,729,139 A | 3/1988 | Nashef | | |
| 4,753,652 A | 6/1988 | Langer et al. | ...................... | 623/1 |
| 4,755,593 A | 7/1988 | Lauren | .......................... | 530/356 |
| 4,770,665 A | 9/1988 | Nashef | | |
| 4,786,287 A | 11/1988 | Nashef et al. | .................. | 8/94.21 |
| 4,838,888 A | 6/1989 | Nashef | .............................. | 623/2 |
| 4,976,733 A | 12/1990 | Girardot | ......................... | 623/11 |
| 5,094,661 A | 3/1992 | Levy et al. | ..................... | 8/94.11 |
| 5,104,405 A | 4/1992 | Nimni | .............................. | 623/2 |
| 5,147,514 A | 9/1992 | Mechanic | ................. | 204/157.68 |
| 5,296,583 A | 3/1994 | Levy | ................................. | 528/72 |
| 5,300,306 A | 4/1994 | Alvarado et al. | ............. | 424/550 |
| 5,332,475 A | 7/1994 | Mechanic | ................. | 204/157.68 |
| 5,368,608 A | 11/1994 | Levy et al. | ..................... | 8/94.11 |
| 5,397,353 A | 3/1995 | Oliver et al. | ....................... | 623/11 |
| 5,413,798 A | 5/1995 | Scholl et al. | | |
| 5,436,291 A | 7/1995 | Levy et al. | ..................... | 524/706 |
| 5,437,287 A | 8/1995 | Phillips et al. | ................. | 128/898 |
| 5,447,536 A | 9/1995 | Girardot et al. | ................ | 8/94.11 |
| 5,476,516 A | 12/1995 | Seifter et al. | ..................... | 8/94.11 |
| 5,509,932 A | 4/1996 | Keogh et al. | ...................... | 623/11 |
| 5,578,314 A | 11/1996 | Cochrum et al. | ............. | 424/424 |
| 5,595,571 A | 1/1997 | Jaffe et al. | ...................... | 8/94.11 |
| 5,607,476 A | 3/1997 | Prewett et al. | | |
| 5,645,587 A | 7/1997 | Chanda et al. | ................... | 623/11 |
| 5,674,298 A | 10/1997 | Levy et al. | ..................... | 8/94.11 |
| 5,679,112 A | 10/1997 | Levy et al. | ..................... | 8/94.11 |
| 5,697,972 A | 12/1997 | Kim et al. | .......................... | 623/2 |
| 5,720,777 A | 2/1998 | Jaffe et al. | .......................... | 623/2 |
| 5,733,339 A | 3/1998 | Girardot et al. | ................ | 8/94.11 |
| 5,746,775 A | 5/1998 | Levy et al. | ..................... | 8/94.11 |
| 5,782,931 A | 7/1998 | Yang et al. | ..................... | 8/94.11 |
| 5,824,067 A | 10/1998 | Gross | ................................. | 623/2 |
| 5,836,313 A * | 11/1998 | Perez et al. | .................... | 128/898 |
| 5,891,196 A | 4/1999 | Lee et al. | ........................ | 8/94.11 |
| 5,911,951 A | 6/1999 | Girardot et al. | | |
| 5,916,265 A | 6/1999 | Hu | | |
| 5,989,498 A | 11/1999 | Odland | ........................... | 422/22 |
| 6,093,530 A | 7/2000 | McIlroy et al. | ................ | 435/1.1 |
| 6,117,979 A * | 9/2000 | Hendriks et al. | ............... | 530/356 |
| 6,166,184 A | 12/2000 | Hendriks et al. | .............. | 530/356 |
| 6,203,755 B1 | 3/2001 | Odland | ........................... | 422/22 |
| 6,251,579 B1 | 6/2001 | Moore et al. | ................... | 435/1.1 |

(Continued)

FOREIGN PATENT DOCUMENTS

EP    0 172 716    8/1985

(Continued)

OTHER PUBLICATIONS

Benz et al. Fundamental and Applied Toxicology (1997) 38: 149-156.*
Registry prinoutout for N,N'-methylenebisacrylamide; Downloaded from STN on Nov. 29, 2009.*
Kanamori et al. Materials Science and Engineering C (2000) 13: 85-89.*
Lutolf et al. Biomacrocolecules (2003; published on the Web Feb. 26, 2003) 4: 713-722.*

(Continued)

*Primary Examiner* — Michael G Wityshyn
*Assistant Examiner* — Susan Hanley
(74) *Attorney, Agent, or Firm* — Katharine A. Jackson Huebsch; Mike Jaro

(57) ABSTRACT

Methods for treating xenogenic tissue for implantation into a human body including in-situ polymerization of a hydrogel polymer in tissue, and tissue treated according to those methods, where the polymerization takes place in tissue that has not been fixed with glutaraldehyde. The polymerization may only fill the tissue, bind the polymer to the tissue, or cross-link the tissue through the polymer, depending on the embodiment. One method includes free radical polymerization of a first vinylic compound, and can include cross-linking through use of a second compound having at least two vinyl groups. Another method utilizes nucleophilic addition polymerization of two compounds, one of which can include PEG and can further include hydrolytically degradable regions. In one embodiment, applicants believe the in-situ polymerization inhibits calcification, and that the polymerization of tissue un-fixed by glutaraldehyde allows for improved penetration of the polymer. The methods find one use in the treatment of porcine heart valve tissue, intended to extend the useful life of the valves by inhibiting calcification. The incorporation of degradable hydrogel regions may initially fill the tissue and reduce any initial inflammatory response, but allow for later infiltration by cells to remodel the tissue.

25 Claims, 11 Drawing Sheets

U.S. PATENT DOCUMENTS

| | | |
|---|---|---|
| 6,506,339 B1 | 1/2003 | Girardot et al. |
| 6,509,145 B1 | 1/2003 | Torrianni |
| 6,521,179 B1 | 2/2003 | Girardot et al. |
| 6,524,327 B1 * | 2/2003 | Spacek .................. 606/214 |
| 2003/0118981 A1 | 6/2003 | Torrianni |
| 2004/0048985 A1 * | 3/2004 | Letchford ................ 525/304 |
| 2004/0093674 A1 * | 5/2004 | Cunanan et al. ........... 8/94.11 |
| 2004/0153145 A1 | 8/2004 | Simionescu et al. |
| 2004/0158320 A1 | 8/2004 | Simionescu et al. |
| 2004/0253291 A1 | 12/2004 | Girardot et al. |

FOREIGN PATENT DOCUMENTS

| | | |
|---|---|---|
| EP | 0 897 942 | 2/1999 |
| WO | 84/01879 | 5/1984 |
| WO | 89/06945 | 8/1989 |
| WO | 01/02031 | 1/2001 |
| WO | 03/064706 | 8/2003 |

OTHER PUBLICATIONS

Khan et al. Synthetic Communications (2000) 30(14): 2599-2608.*

Civerchia-Perez et al. Proc. Natl. Acad. Sci. (1980) 77(4): 2064-2068.*

Shanthi C. et al, "Regulation of Biocalcification of Bovine Pericardial Tissue by Grafting Poly(Glycidyl Methacrylate-butylacrylate) Copolymers," J Bioact Compat Pylom; Journal of Bioactive and Compatible Polymers, Oct. 1997, vol. 12, No. 4, pp. 308-320.

Abstract of Shen, et al, "Proteins and bioprosthetic calcification in the rat model," J Heart Valve Dis. Jan. 1996; 5(1): 50-7.

Abstract of Sofos, et al, "Nonacid meat decontamination technologies: model studies and commercial applications," Int J Food Microbiol. Nov. 10, 1998; 44(3):171-88.

* cited by examiner

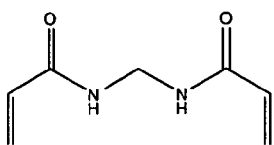
N,N'-methylenebisacrylamide
*(Structure 7)*
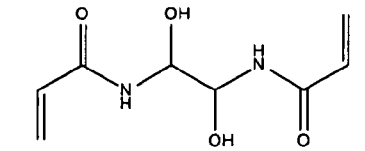
N,N'-(1,2-dihydroxyethylene)bisacrylamide
*(Structure 8)*
n=1, 2, 3...of integer
Polyethyleneglycol divinyl ether
*(Structure 9)*
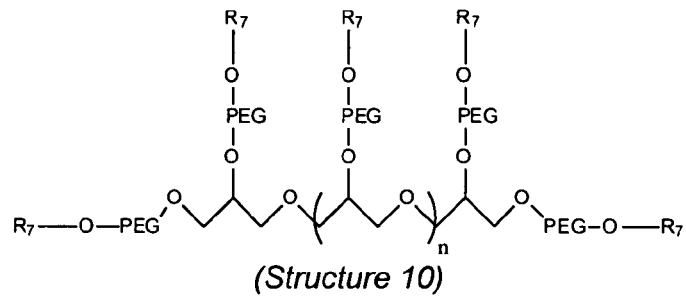
*(Structure 10)*
FIG. 3

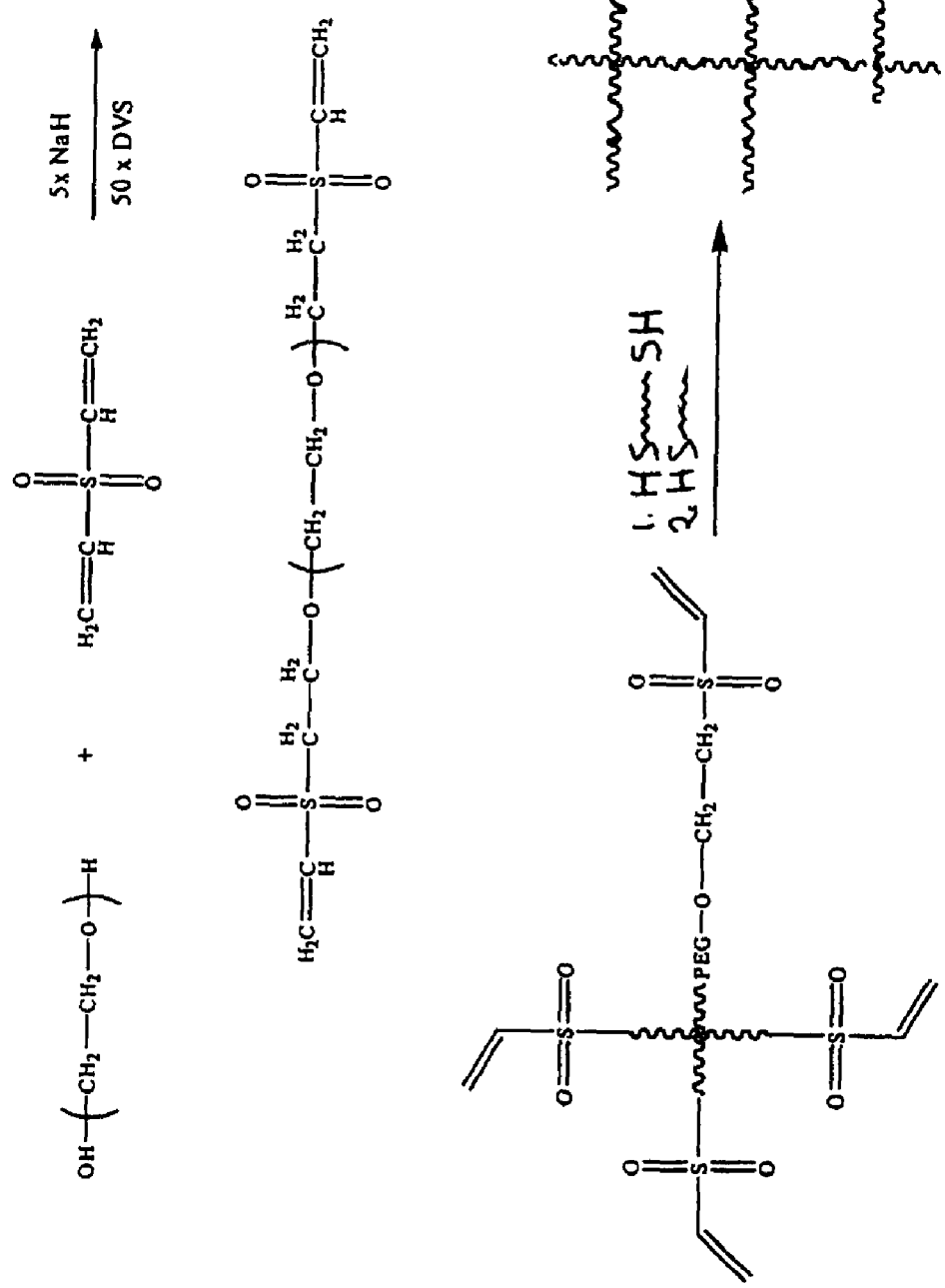

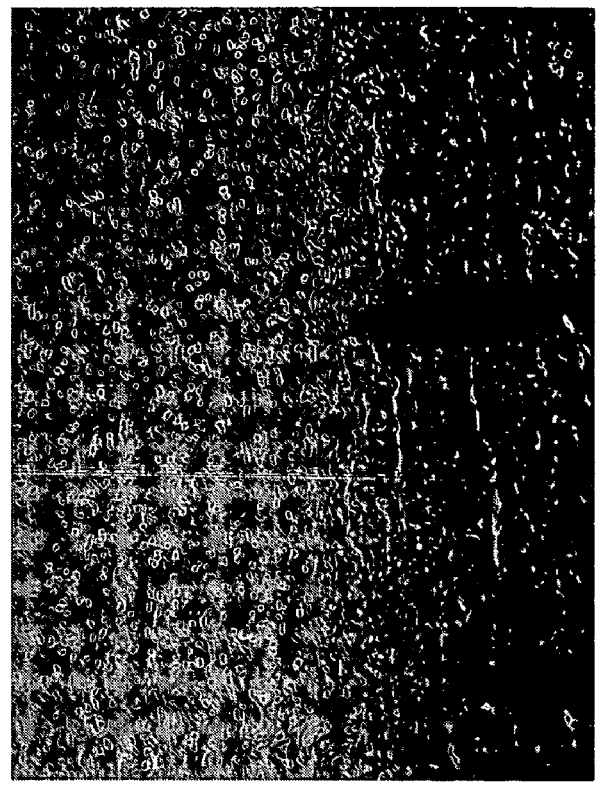
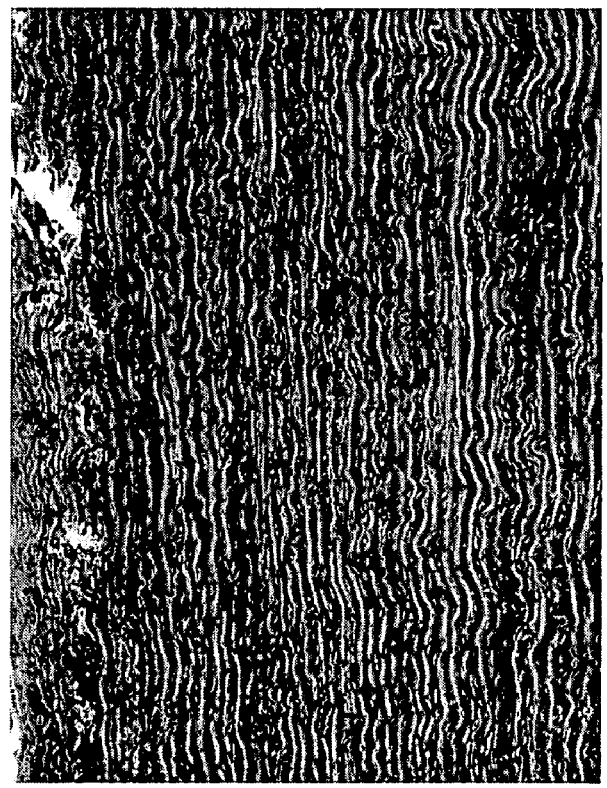
FIG. 7B
FIG. 7A

|  | Fresh | Fresh + AAm Example 1 | 0.2% GA | 0.2% GA+AAm Example 2 | Fresh + HEMA Example 3 | Fresh + propional + AAm Example 8 |
|---|---|---|---|---|---|---|
| ST | 67.2±0.3 | 73.3±1.0 | 90.6±0.1 | 92.7±0.6 |  | 64.1±1.0 |
| RDP | 21.5±0.5 | 39.7±3.5 | 42.7±1.9 | 76.7±2.3 | 36.0±1.8 | 30.3±1.2 |
| RAC | 147.6±8.5 | 99.8±4.6 | 54.9±1.5 | 55.8±1.2 | 110.8±6.8 | 48.3±2.1 |
| Stress (MPa) | 0.06±0.002 | 0.40±0.02 | 0.63±0.05 | 0.45±0.01 | 0.187±0.013 | 0.33±0.04 |
| Calcium (µg/g) |  | 12.5±5.3 | 97.4±5.3 | 94.4±7.9 | 6.8±0.2 | 10.7±4.6 |

ST: shrinkage temperature, degrees Celsius

RDP: Resistance toward degradation by protease (% tissue remaining after degradation; based on tissue mass only (hydrogel mass discounted)

RAC: Residual amine content (µmol/g);

Stress: measured at 25% strain (MPa), with higher stress indicative of greater stiffness.

FIG. 10

BIOPROSTHETIC TISSUE PREPARATION WITH SYNTHETIC HYDROGELS

This application claims the benefit of U.S. Provisional Application No. 60/515,618 filed Oct. 30, 2003. The entire contents of that provisional application are herein incorporated by reference.

FIELD OF THE INVENTION

The present invention is related generally to medical devices. More specifically, the present invention is related to methods for treating tissue for implantation by filling the tissue with hydrogels. The present invention can be used to treat porcine heart valves prior to implantation in humans, which can reduce calcification after implantation.

BACKGROUND OF THE INVENTION

Xenogenic tissue generally requires preservation prior to implantation in human beings. Without prior treatment, the tissue is rapidly enzymatically degraded and can elicit a severe immunological response. A large number of fixation techniques have been applied to xenogenic tissue in order to render it suitable for human implantation. The most common method involves the cross-linking of the tissue with glutaraldehyde (GA). Fresh tissue, without GA fixation, is destroyed after implantation by degradative enzymes. A common example of xenogenic tissue is Bio-Prosthetic Tissue (BPT), for example, porcine heart valve tissue, harvested from pigs, treated, and implanted into humans requiring new heart valves. The most common method used to treat BPT prior to implantation is treatment using glutaraldehyde fixation. The glutaraldehyde, having two aldehyde functionalities, can react with a tissue amino group at each end, thereby cross-linking the tissue, and rendering the tissue resistant to enzymatic degradation.

The use of GA fixed porcine heart valves was initially viewed as very promising to young heart valve recipients, as the BPT valves did not require the lifetime regimen of taking anti-coagulant and blood thinning drugs. However, GA fixed tissue proved subject to calcification, with implanted porcine heart valves often lasting only 10-15 years. Higher concentrations of GA may be used to decrease calcification, but this typically results in increased tissue stiffness. GA, while beneficial and commonly used for tissue fixation, also has a slight cytotoxic effect, and can also have an inflammatory effect.

Some researchers have attempted to modify bioprosthetic tissue with hydrogels. Applicants believe that many or all previous methods are limited by relying upon conventional GA cross-linking as an initial step. The GA cross-linking may link to most or all available amino groups in the tissue.

Attempts have been made to fill the GA fixed BPT tissue with a polymer, in order to reduce calcification. In particular, an attempt has been made to perform in-situ polymerization of acrylic acid monomers, to form the hydrogel poly acrylic acid in BPT tissue. See Nashef, U.S. Pat. Nos.: 4,729,139; 4,481,009; and 4,770,665.

Applicants believe that the dense GA cross-linked tissue does not allow for sufficient penetration of the hydrogel monomer molecules. Applicants believed that if tissue is initially fixed and thereby stiffened by GA cross-linking, then further filling with polymers might further stiffen the tissue, possibly making the tissue too stiff to serve some purposes, for example, as heart valve leaflets.

What would be desirable are methods for treating xenogenic tissue that resists calcification, resists initial biodegradation by matrix metalloproteases (MMPs), limits infiltration by inflammatory cells, elicits minimal immunogenic response, and does not increase tissue stiffness to a point rendering the implanted tissue unsuitable for its intended purpose.

SUMMARY OF THE INVENTION

The present invention provides methods for treating xenogenic tissue for implantation into a human body. The methods can include in-situ polymerization of a hydrogel polymer in tissue, and tissue treated according to those methods, where the polymerization takes place in tissue that may have not been fixed with glutaraldehyde. The resulting filled tissue has a hydrogel polymer matrix that occupies the interstitial spaces and is believed to deny access to Calcium, MMPs, inflammatory cells and antigens. The polymerization may only fill the tissue, bind the polymer to the tissue, or cross-link the tissue through the polymer, depending on the embodiment. Methods provided by the present invention have shown significantly reduced calcification of tissue in animal studies, compared to GA fixed tissue, while providing degradation resistance and reduced stiffness.

One method includes free radical polymerization of a first vinylic compound, and can include cross-linking through use of a second compound having at least two vinyl groups. Another method utilizes nucleophilic addition polymerization of two compounds, one of which can include polyethylene glycol (PEG) and can further include hydrolytically degradable regions. Applicants believe the in-situ polymerization inhibits calcification, and that the polymerization of tissue un-fixed by glutaraldehyde allows for improved penetration of the polymer. The methods find one use in the treatment of porcine heart valve tissue, intended to extend the useful life of the valves by inhibiting calcification. In one method, the incorporation of degradable hydrogel regions initially fills the tissue and reduces any initial inflammatory response, but allows for later infiltration by cells to remodel the tissue.

One method utilizes free radical polymerization to perform the in-situ polymerization. A tissue can be provided, where the tissue has unreacted amino groups. A first compound having at least one vinyl moiety can then be introduced into the tissue and polymerized in the tissue to form a hydrogel polymer. The polymerization may include reacting the vinyl moiety with the tissue amino groups to bind at least some of the polymer to the tissue amino groups at one or more sites per polymer, depending on the embodiment. The method may further include providing a second compound that is different from the first compound, where the polymerizing includes reacting the second compound to cross-link the polymer.

Another method according to the present invention utilizes nucleophilic addition polymerization to perform the in-situ polymerization. A first compound having at least two $\alpha, \beta$ unsaturated moieties, and a second compound having at least two nucleophilic moieties can be provided and introduced into the tissue. Polymerization can be initiated to polymerize the first and second compounds through conjugate nucleophilic addition, to form a hydrogel polymer.

The nucleophile can be selected from the group consisting of amino and thiol groups. The first or second compound can include water soluble polymers, for example, polyethylene glycol(PEG), polyvinyl alcohol(PVAL), polyvinylpyrrolidone(PVP), polyacrylamide(PAM), and polyacrylic acid (PAA), and random, graft, and block copolymers formed thereof. The first or second compound can also include hydrolytically degradable polymers, polyesters, polyglycolic acid, polylactic acid, polycaprolactone, polyhydroxybuterate, polyortoesters, polyanhydrides, poly(sebasic acid-hexadecanoic acid anhydride), polyiminocarbonates, and random, graft, and block copolymers formed thereof. In some methods, the first or second compound includes polymers selected from the group consisting of hydrolytically degradable polymers, polyamino acids, and polysaccharides, and random, graft, and block copolymers formed thereof. Some $\alpha$, $\beta$ unsaturated moieties include vinyl sulfone groups or acrylate groups.

In some methods, in which the tissue has unreacted nucleophilic moieties, the polymerization includes reacting the $\alpha$, $\beta$ unsaturated moieties with the tissue nucleophilic moieties to bind at least some of the polymer to the tissue nucleophilic moieties.

In some methods, the first and/or second compound includes polyethylene glycol (PEG). The PEG resides in a compound backbone in some methods and in a compound sidearm in other methods. Some $\alpha$, $\beta$ unsaturated moieties include between 2 and 8 arms having polyethylene glycol, and also include vinyl sulfone groups or acrylate groups.

In various methods, none, essentially none, or only a minority of the tissue amino groups are cross-linked with glutaraldehyde. In some methods, any glutaraldehyde fixation is done after the polymerization.

The present invention can include using capping to control the stiffness of the tissue. A block capping agent can be used to limit the participation of either amino or carboxyl groups in either the in-situ polymerization or in any glutaraldehyde or other fixation method. The block capping can leave essentially non-reactive groups coupled to the tissue. Some block capping agents react with tissue amino groups through aldehyde or epoxy moieties. Examples of amino block capping agents include glycidyl ether (PGE), glyceral, propional, ethanal, ethanol, propanal, and butanal. Activation capping can be used to increase the participation of amino and/or carboxyl groups in the in-situ polymerization. The activation capping can include reacting an epoxy moiety with the amino or carboxyl group. The activation capping can also include leaving a vinyl moiety or an alpha, beta unsaturated moiety free to participate in the in-situ polymerization reaction.

In some methods according to the present invention the tissue was decellularized prior to polymerization. The decellularizing can include treating the tissue with a surfactant to rupture the cell membranes, followed by rinsing the tissue to remove cell membrane, lipid, loose connective material, and other components. The decellularized material remaining includes a collagen scaffold. Performing the in-situ polymerization on decellularized tissue can be particularly advantageous in the polymerization of large molecular weight monomers or prepolymers through nucleophilic addition.

The present invention provides tissue products treated by all the methods described in the present application. One family of tissue products includes porcine heart valves treated using the invention methods prior to implantation in the human body. One heart valve includes xenogenic tissue, wherein the tissue has native amino groups, the tissue including a plurality of hydrogel polymers disposed within the tissue, wherein at least some of the polymers are directly covalently bonded to the native amino groups. In some heart valves, the polymer is formed from monomers or prepolymers including vinyl groups, where the covalent bond between the polymer and the tissue amino group is a reaction product of a free radical polymerization between the vinyl group and the tissue amino group. In other heart valves, the polymer is formed from monomers or prepolymers including alpha, beta unsaturated groups, where the covalent bond between the polymer and the tissue amino group is a reaction product of a nucleophilic addition polymerization between the alpha, beta unsaturated groups and the tissue amino group. In some heart valves, at least some of the polymers are directly covalently bonded to at least two tissue native amino groups.

DESCRIPTION OF THE DRAWINGS

FIG. 3 is a set of chemical structures for Type 2 monomers, having two vinyl groups;

FIG. 6 includes chemical structure diagrams illustrating reaction mechanisms for forming a hydrogel polymer;

FIG. 7A is a photomicrograph of fresh tissue, not treated with GA, after in-situ polymerization with acrylamide monomer and bis-acrylamide cross-linker, after H&E staining, showing substantial polymer penetration into the tissue;

FIG. 7B is similar to FIG. 7A, but with the tissue having been fixed with GA prior to in-situ polymerization, showing substantially reduced polymer penetration relative to FIG. 7A;

FIG. 10 is a table summarizing the experimental results of several examples of the invention;

DETAILED DESCRIPTION OF THE PREFERRED EMBODIMENTS

Figure 1:
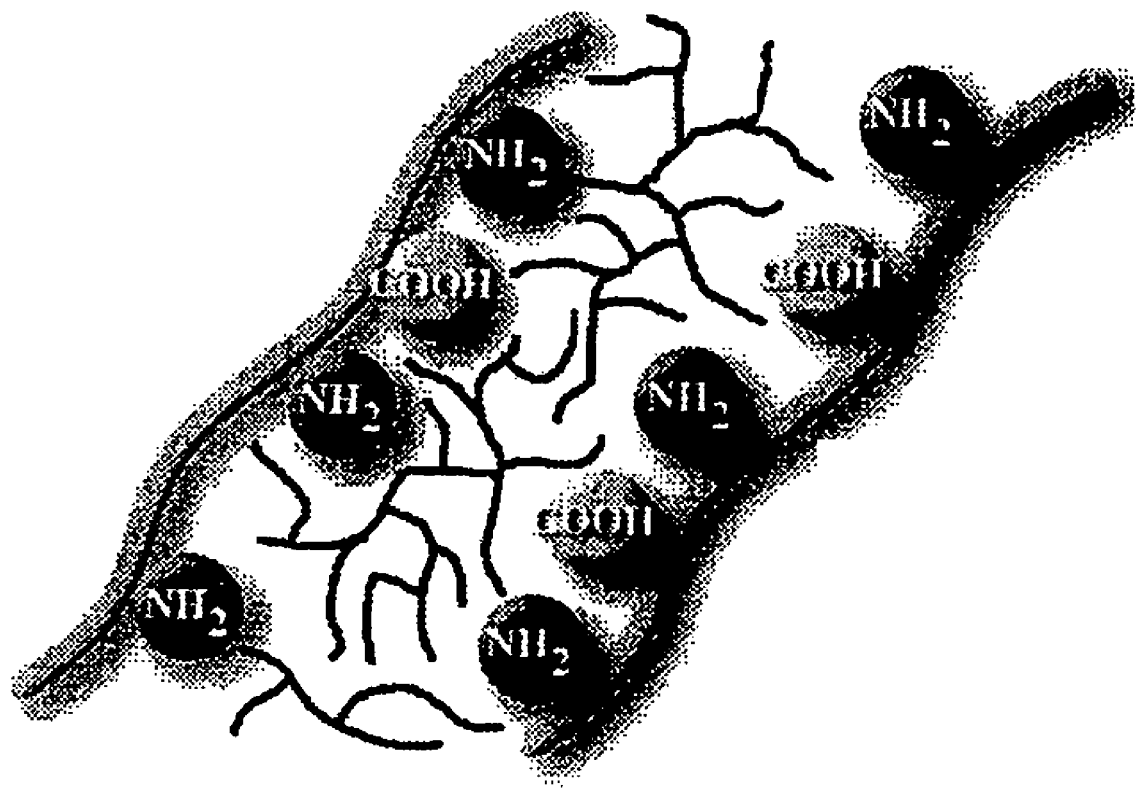
FIG. 1 is a highly diagrammatic cross-sectional view of tissue filled through in-situ polymerization.

FIG. 1 illustrates a piece of tissue in a highly diagrammatic cross-section. The tissue includes native carboxyl groups and amino groups, indicated by COOH and NH2 in FIG. 1. The present invention provides methods for tissue filling and tissue cross-linking using in-situ polymerization. The polymer resulting from the in-situ polymerization is represented by the network polymer structure in FIG. 1. The polymer may be bound at none, one, or multiple sites to the tissue, depending on the embodiment of the invention utilized. Some of the COOH and/or NH2 groups may be capped or inactivated using block capping groups (not shown in FIG. 1). The polymer may be directly covalently bound to the tissue or bound through activation capping groups (not shown in FIG. 1), depending on the embodiment.

One method used to cross-link and fill tissue includes providing the tissue, where the tissue has unreacted amino groups. A first monomer can be provided, where the first monomer has at least one vinyl moiety.

Type 1: Monomers Containing One Vinyl Group

Examples of some monomers having a single vinyl moiety are shown below in structures 1 through 6. Structure 1 shows the general structure of a vinylic monomer. Preferred monomers include those with side-groups listed in structures 2 through 6, as well as any other essentially water-soluble monomers suitable for the formation of hydrogels.

(Structure 1)

Monomers of structure 1 where $R_1$=H, $R_2$=H, $R_3$=H or $CH_3$ and $R_4$=

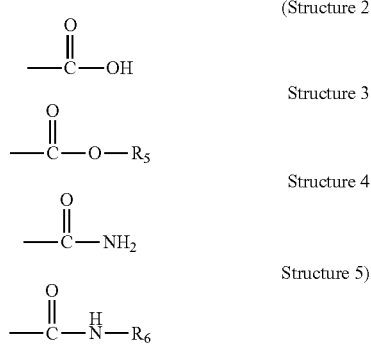

(Structure 2)

Structure 3

Structure 4

(Structure 5)

where $R_5$ and $R_6$ includes:

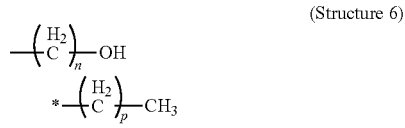

(Structure 6)

n = 1, 2, 3...of integer
p = 0, 1, 2...

Figure 2:
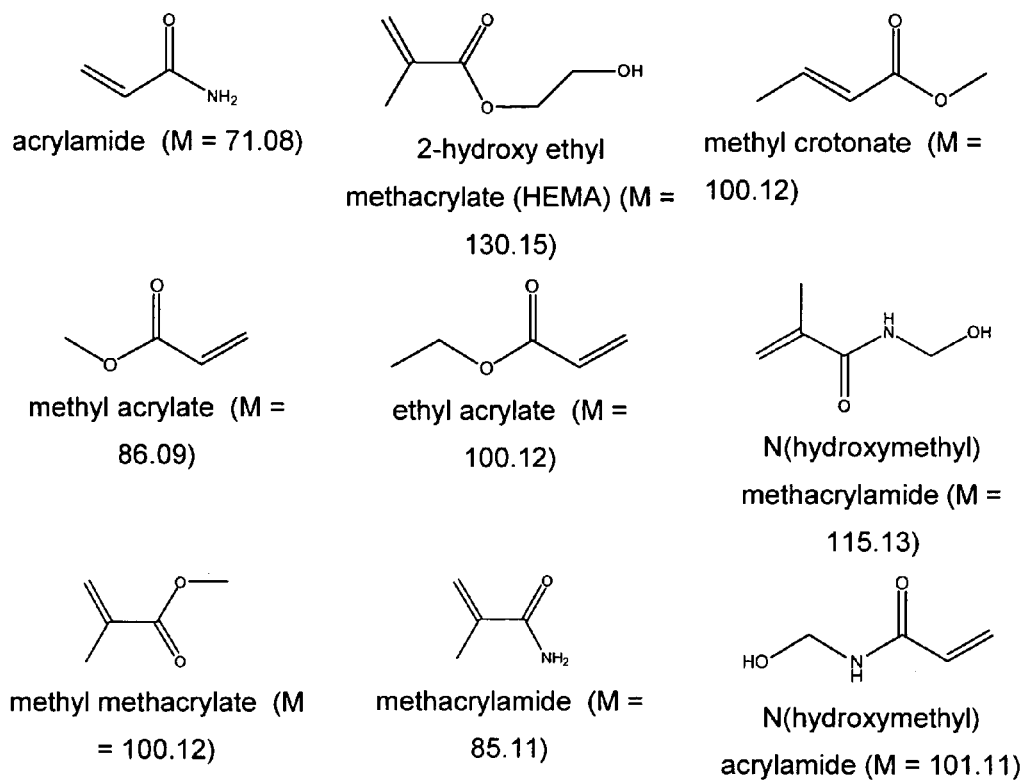
FIG. 2 is a set of chemical structures for Type 1 monomers, having one vinyl group.

FIG. 2 shows some specific examples of Type 1 monomers, including specifically: acrylamide; 2-hydroxy ethyl methacrylate (HEMA); methyl crotonate; methyl acrylate; ethyl acrylate; N(hydroxymethyl) methacrylamide; methyl methacrylate; methacrylamide; and N(hydroxymethyl) acrylamide.

The monomer can be introduced or infused into the tissue. In one method, the monomer solution is introduced by soaking or immersing the tissue in the monomer, followed by removing the tissue from the monomer solution. The tissue can be soaked for between 1 and 72 hours in one embodiment, and for about 24 hours in another embodiment. Free radical polymerization can be initiated using any suitable initiator known to those skilled in the art. Initiators include thermal initiators, peroxy compounds, azo compounds, photo initiators, redox initiators, and radiation induced initiators. Examples of specific reaction conditions are described in detail below.

The resulting free radical polymerization can covalently bond a monomer vinyl moiety directly to a tissue amino group, followed by further polymerization, followed by another covalent bond formed between the polymer and a tissue amino group, thereby cross-linking the tissue. The monomers are preferably those that lead to the formation of a hydrogel polymer.

FIG. 3 illustrates that the present invention can also include using a monomer having more than one vinyl group. Monomers having more than one vinyl group can be used to form three-dimensional linked polymers. Monomers having more than one vinyl group can also be used to cross link the polymer formed by monomers having a single vinyl group, and render the polymer insoluble. Examples of monomers having more than one vinyl functionality are listed as Type 2 monomers, having structures 7 through 10 in FIG. 3.

In one method, the tissue is soaked in a solution of at least 20 percent acrylamide, more preferably at least 25 percent, and most preferably at least about 30 percent acrylamide. In one method, 30 percent acrylamide is used, together with a bisacrylamide cross linker and an initiator. The tissue can be soaked for at least 12 hours, more preferably at least 18 hours, and most preferably at least about 20 hours. The tissue can then be removed from solution, the excess monomer removed by blotting, and the tissue polymerization initiated by application of UV light.

In another method, a solution containing both acrylamide and hydroxymethacrylate (HEMA), together with a bisacrylamide cross linker and an initiator is used to soak the tissue for the time periods discussed in the previous paragraph. In some methods, the weight percent of the acrylamide and HEMA total at least 20 percent, more preferably 25 percent, and most preferably at least about 30 percent. In one method, the solution contains about 15 weight percent acrylamide and 15 weight percent HEMA.

Type 2: Monomers Containing More than One Vinyl Group

FIG. 3 illustrates examples of type 2 monomers, having more than one vinyl group. The examples include: N, N'-methylenebisacrylamide, N, N'-(1,2-dihydroxyethylene) bisacrylamide, polyethyleneglycol divinyl ether, and $R_7$—O—PEG-O—C(—C—O-PEG-O—$R_7$)CO[C(—C—O-PEG-O—$R_7$)CO—]$_n$C(—C—O-PEG-O—$R_7$)CO—PEG-O$R_7$, where $R_7$ contains a vinyl group and n is an integer 1 or greater.

Initiation of monomers of Type 2 will result in cross-linked polymer. Thus, they can be used on their own, or as cross-linking copolymers with Type 1 monomers. It may also be desirable to use mixtures of two or more monomers to fill the tissue with copolymers. In this way certain desired characteristics may be imparted to the filling material. Monomers of Type 2 can also be used as a minor component in mixtures with Type 1 monomers to act as cross-linking agents.

The tissues cross-linked via in-situ polymerization are preferably not fixed with glutaraldehyde. The tissues have essentially no glutaraldehyde, with the term "essentially" having the same meaning in this context as the in the transition phrase "consisting essentially of", that is, not enough glutaraldehyde to materially effect the basic and novel characteristics of the tissue. In a preferred embodiment, substantially all of the tissue amino groups are not cross-linked with glutaraldehyde. In some methods, the tissue is not treated with glutaraldehyde either before or after in-situ polymerization. In other methods, the tissue is treated with glutaraldehyde only after in-situ polymerization.

As shown in structures 9 and 10 of FIG. 3, some embodiment monomers include polyethylene glycol (PEG). Some embodiments include the PEG in a monomer backbone while other embodiments include PEG in a monomer sidearm. If n is equal to 4, then structure 10 would have 8 sidearms.

Figure 4A:
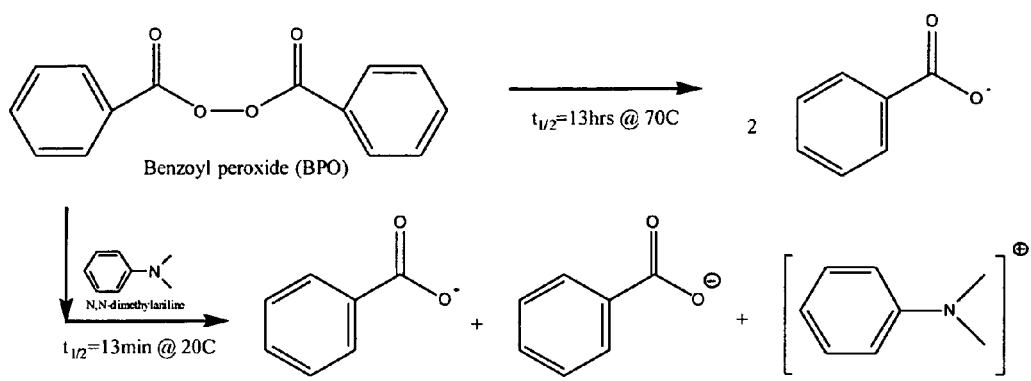
FIGS. 4A, 4B, and 4C are sets of chemical structures for polymerization initiators.
Figure 4B:
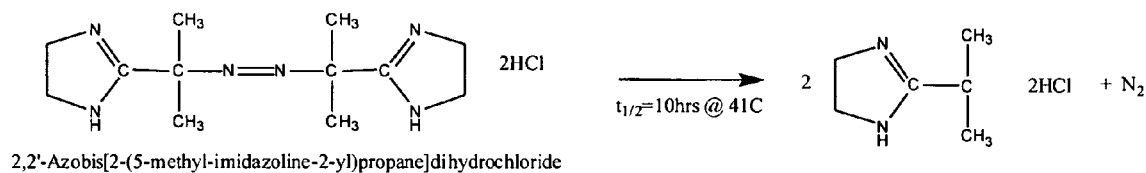
Figure 4C:
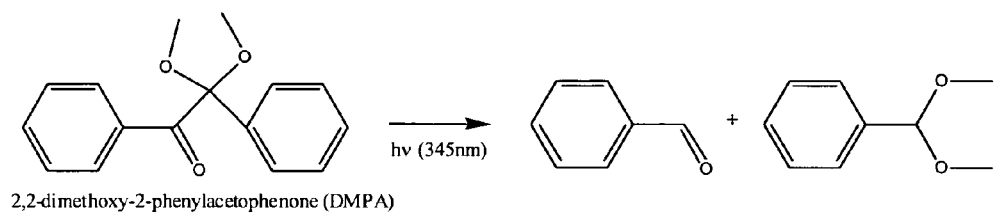

FIGS. 4A, 4B, and 4C show that free radical initiators used to initiate polymerization can include thermal initiators, peroxy compounds, azo compounds, photo initiators, redox initiators, and radiation induced initiators, including those illustrated below.

Peroxy compounds: Peroxides, hydroperoxides, peracids, peresters, percarbonates, peroxylates, diketals, ketone peroxides, e.g. benzoyl peroxide; t-butyl hydroperoxide. See, for example, the benzoyl peroxide mechanism illustrated in FIG. 4A.

Compounds with the ability to increase the rate of dissociation and thus radical production, termed "kickers" may be employed to lower the initiation temperature. N,N-dimethylaniline is used to demonstrate the principle only; aromatic amines are known carcinogens.

Azo compounds: Azonitriles, azoesters, e.g. azobis(isobutyronitrile); 2,2'-Azobis[2-(5-methyl-imidazoline-2-yl) propane]dihydrochloride; 2,2'-Azobis(2-methylpropionamide) dihydrochloride. See, for example, the 2,2'-Azobis[2-(5-methyl-imidazoline-2-yl) propane]dihydrochloride mechanism illustrated in FIG. 4B.

Photoinitiators: Azo and peroxy-compounds, acetophenones, benzophenones, acylphosphonates, diketones. e.g. 2,2-dimethoxy-2-phenylacetophenone (DMPA). See the 2,2-dimethoxy-2-phenylacetophenone (DMPA) mechanism illustrated in FIG. 4C.

Redox initiators include for example.:
reducing agents with peroxides: e.g. $Fe^{2+}+H_2O_2 \rightarrow Fe^{3+}+HO^-+HO\cdot$; and
reducing agents persulfates: $Fe^{2+}+S_2O_8^{2-} \rightarrow Fe^{3+}+SO_4^{2-}+SO_4^-\cdot$.

EXAMPLES OF REACTIONS

Figure 5A:
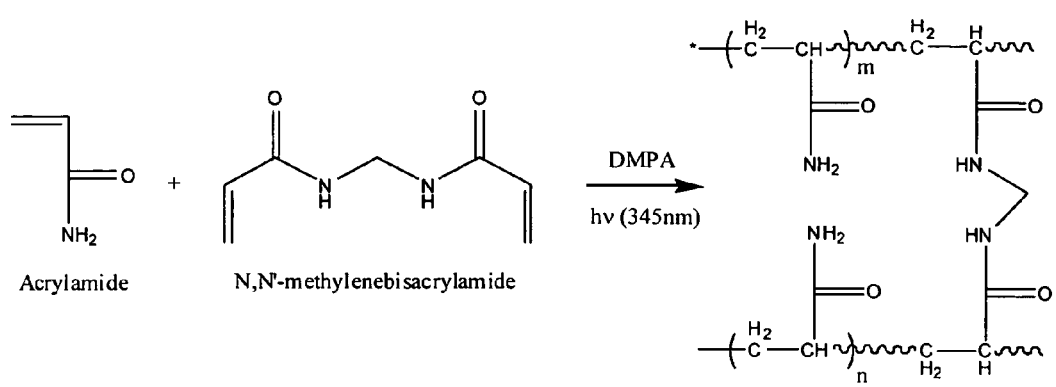
FIGS. 5A and 5B are reaction mechanisms for polymerization of Type 1 and Type 2 monomers, respectively.
Figure 5B:
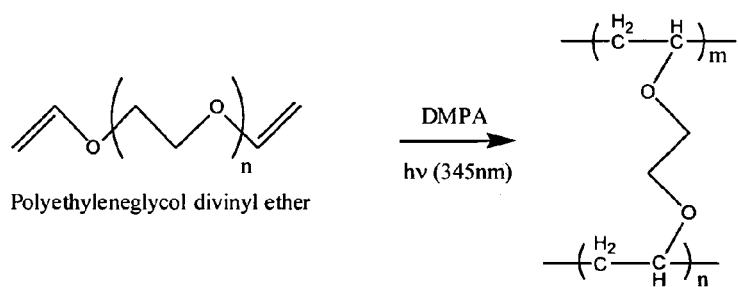

Referring now to FIGS. 5A and 5B, one example of a reaction is a Type 1 monomer plus a crosslinking monomer plus a light sensitive initiator: The filling of tissue with a solution containing a vinyl monomer (acrylamide), together with a smaller quantity of a crosslinking monomer (N, N-methylenebisacrylamide) and a light sensitive initiator (DMPA), followed by exposure to UV light, constitutes one preferred embodiment. FIG. 5A illustrates one reaction, of acrylamide with N, N'-methylenebisacrylamide, having DMPA as an initiator.

FIG. 5B illustrates another reaction, of a Type 2 monomer using a light sensitive initiator, specifically polyethyleneglycol divinyl ether and DMPA.

Nucleophilic Addition Polymerization

The in-situ polymerization can also be accomplished using nucleophilic addition rather than free radical polymerization. In this method for treating a tissue for implantation into a human body the tissue has unreacted amino groups as with the free radical polymerization method. A first compound is provided, having α (alpha), β (beta) unsaturated moieties. A second compound is provided, having nucleophilic moieties. The first and second compounds can be introduced into the tissue and polymerized through conjugate nucleophilic addition, to form a hydrogel polymer. The polymer thus formed may simply fill the tissue and not be bonded, or be singly or multiply bonded to the tissue. Even where the polymer thus formed is not significantly bonded to the tissue, the use of nucleophilic addition polymerization allows the incorporation of specific polymers or oligomers, allowing for hydrolytically degradable regions to be incorporated into the hydrogel polymer.

The polymerization may include reacting the α (alpha), β (beta) unsaturated moiety with the tissue groups to covalently bond at least some of the polymer to the tissue. In one embodiment, the α, β unsaturated moiety forms a covalent bond to a tissue nucleophile, for example a tissue hydroxyl, amino, or thiol group. The polymerization can continue, with another portion of the polymer eventually forming at least one other covalent bond to another tissue reactive group.

Michael additions are a specific class of conjugate nucleophilic additions (addition of enolate ions to α, β unsaturated carbonyl compounds).

One embodiment of the current invention teaches the use of the general reaction in the filling of bioprosthetic tissue:

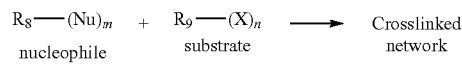

where
X represents an α, β-unsaturated compound, generally with the form —Z—C=C, where Z includes CHO, COR, COOR, $CONH_2$, CN, SOR, $SO_2R$.
Nu represents a nucleophile, typically amino (—$NH_2$) or thiol (—SH) groups.
$R_8$ and $R_9$ represent a monomeric or more preferably polymeric species
$R_8$ and $R_9$ may include water-soluble polymers such as polyethylene glycol (PEG), polyvinylalcohol (PVAL), polyvinylpyrrolidone (PVP), polyacrylamide (PAM), polyacrylic acid (PAA), and other polymers known to those practiced in the art, as well as random, graft and block copolymers thereof.
$R_8$ and $R_9$ may further include polymers that are hydrolytically degradable, e.g. polyesters (polyglycolic acid, polylactic acid, polycaprolactone, polkyhydroxybuterate, polyortoesters etc), polyanhydrides (poly(sebasic acid-hexadecanoic acid anhydride)), polyiminocarbonates, etc.
$R_8$ and $R_9$ may further include the biologically derived polymers such as polyamino acids and polysaccharides that may be enzymatically degradable.
m and n are integers such that
$m \geq 2$ and $m \geq 2$ and $m+n>4$ Monomer/Pre-Polymer Examples As mentioned, $R_9$ may be monomeric or polymeric in form. Thus the following are all possible examples of suitable moieties. Structures 7, 8, 11, and 12 can be polymerized using either free radical or nucleophilic addition polymerization.

monomeric

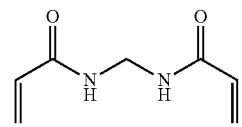

(Structure 7)

-continued

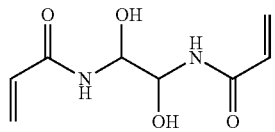
polymeric (Structure 8)

(Structure 11)

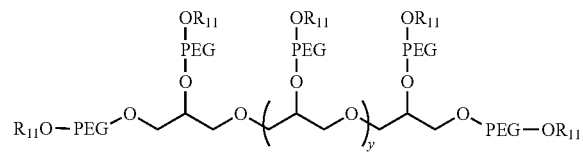

(Structure 12)

where $R_{10}$ and $R_{11}$ have the form —Z—C=C, where Z includes CHO, COR, COOR, $CONH_2$, CN, SOR, $SO_2R$.

PEG=polyethylene glycol

Crosslinker Examples

Examples of chemically stable (e.g. structure 13) and enzymatically degradable crosslinkers (structure 14) are given. Other examples of stable crosslinkers include ethanedithiol, dithiothreitol, and analogs.

(Structure 13)

(Structure 14)

$H_2N$—$(AA)_n$—COOH where $R_{12}$ is or contains a nucleophile, e.g. a thiol or amino group Structure 14 represents oligo or polypeptide sequence with AA representing any one of the naturally occurring or synthetic amino acids, at least two of which contain a amino-, or more preferable thiol groups at or near the termini of the sequence. Structure 14 can be used to cross-link structure 12 through nucleophilic addition, by reaction of the thiol groups of structure 14 with the R11 groups of structure 12.

EXAMPLES OF REACTIONS

Vinyl Sulfone Derivatized PEG+PEG Dithiol

Chemically stable hydrogels may be produced by reacting chemically stable precursor substrates (e.g. structure 15; vinyl sulfone derivatized multi-arm PEG) with chemically stable nucleophilic crosslinkers (e.g. structure 16; PEG-dithiol). Two to eight arm vinyl sulfone derivatized PEGS, having, for example, pentaerythritol or sorbitol cores may also be used.

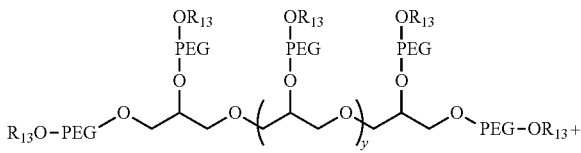

(Structure 15)

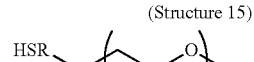

Crosslinked Network (Structure 16)

where

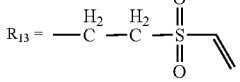

Acrylated PEG+Crosslinker

In addition to using hydrolytically degradable substrates and/or crosslinkers, hydrolytic degradability may also be imparted by using a hydrolytically degradable bond between the precursor substrate and the crosslinker. Two to eight arm acrylated PEGS, having, for example, pentaerythritol or sorbitol or cores may also be used. See also, for example, structure 15.

If R13 in structure 15 were an acrylate instead of a vinyl sulfone group, the reaction product between structures 15 and 16 would be hydrolytically unstable due to the hydrolytically cleavable ester bond formed.

Combinations for Degradability

Both hydrolytic and enzymatic degradability may be imparted by using various combinations of substrate and crosslinker, i.e. hydrolytic degradability of any one of the substrate, crosslinker or bond will impart hydrolytic degradability, whereas enzymatic degradability of either the substrate or the crosslinker will render the hydrogel enzymatically degradable. Clearly, if both enzymatic and hydrolytically degradable elements are present, the hydrogel will be degradable by both (hydrolytic and enzymatic) mechanisms.

Capping Agents

The present invention also provides methods for preventing tissue reactive groups from reacting by capping the tissue reactive groups with essentially non-reactive species. Capping may also be used to introduce added functionality to the tissue through activation capping, which can increase the participation of amino or carboxyl groups in tissue crosslinking. The stiffness of the treated tissue may be increased by increasing the participation of the tissue in cross-linking, and may be decreased by decreasing the participation of the tissue in cross-linking.

As used herein, the term "Tissue Capping" refers to the chemical attachment of monomeric or polymeric compounds to reactive groups present in bioprosthetic tissue (amino, carboxyl, thiol, guanidine, hydroxyl etc), and may be either block capping or activation capping. Block capping refers to blocking the reactive side-chain groups from any further chemical reaction in subsequent tissue processing steps. Activation capping refers to introducing added functionality to the tissue, thereby enabling or enhancing further chemical reaction in subsequent tissue processing steps. In some embodiments, some or all of the amino groups of the tissue are bound prior to introducing the monomer, thereby eliminating subsequent reaction of the amino with the monomer. In other embodiments, some or all of the carboxylic acid groups of the tissue are bound prior to introduction of the monomer. In still other embodiments, both amino and carboxyl groups are capped prior to introducing the monomer.

Thus, by selectively capping the reactive side chains, the chemical reactivity of the tissue in the subsequent filling steps may be controlled.

where BPT=Bio-Prosthetic Tissue, X represents a reactive group in the tissue, and Y represents a group capable of forming a covalent bond with X. The bond may be achieved either by the groups being inherently reactive toward one another, or by activation of either X or Y with suitable activating agents. $R_{17}$ represents the remaining part of the capping molecule (to be further defined in sections below).

Capping Examples

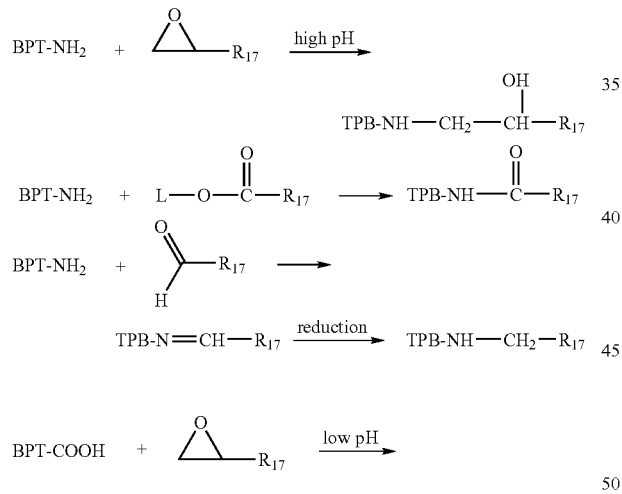

where L represents a leaving group, e.g. N-Hydroxysuccinimide (NHS).

Block Capping

In order to block reactive groups in the tissue from participating in reactions during tissue filling, $R_{17}$ must not be susceptible toward nucleophilic or free-radical attack, nor itself be able to act as an effective nucleophile toward the filling monomers/polymers.

Thus block capping compounds may include:

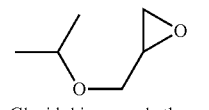

Glycidyl isopropyl ether
(PGE)

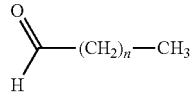

n = 0, 1, 2, 3...
(ethanal, propanal, butanal etc)

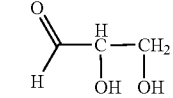

Glyceral

Activation Capping

The term "activation capping" refers to the covalent attachment onto the BPT of di- or multifunctional compounds, containing at least one group capable of reacting with the tissue and at least one group capable of free-radical polymerization in subsequent filling steps. For example, the structures below are capable of addition to amino and carboxyl groups via their epoxy functionalities, and further capable of free-radical polymerisation (with or without the additional presence of another vinylic monomer)

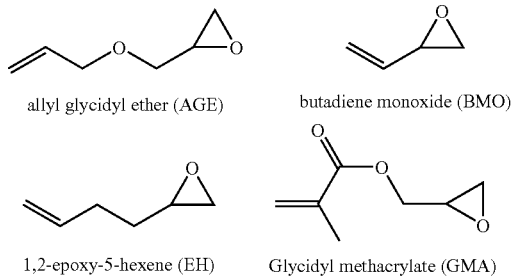

allyl glycidyl ether (AGE)   butadiene monoxide (BMO)

1,2-epoxy-5-hexene (EH)   Glycidyl methacrylate (GMA)

Tissue Pre-Treatment

The methods described in the present application, i.e. filling, capping and crosslinking may be performed on standard BPT or BPT that has undergone decellularization. This process can involve the removal of cellular material from the tissue with surfactants. In addition to removing cells and other material from the BPT, the decellularization process renders the tissue more "porous", thus allowing for the more rapid insudation of monomers, and also for the insudation of larger monomers or prepolymers that may not have penetrated non-decellularized tissue. Decellularization of tissue is described in U.S. Pat. No. 6,509,145, herein incorporated by reference.

Hydrogel Example

FIG. 6 illustrates one mechanism using Michael addition to form a hydrogel. A prepolymer can be formed from PEG and vinyl sulfone. The prepolymer containing PEG and end vinyl sulfone groups can be reacted with nucleophiles, including di-nucleophiles, for example, thiols and di-thiols, represented by

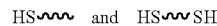

in FIG. 6, respectively.

EXPERIMENTAL RESULTS

Example 1

AAm+bAAm

Fresh porcine heart valve tissue was rinsed in a buffered saline solution. The tissue was subsequently removed from the buffered saline, and placed in a fresh buffered saline solution containing acrylamide (AAm; 30 g/100 ml), N, N'-methylene bisacrylamide (bis-AAm: AAm ratio=1:36.5) and 2,2-dimethoxy-2-phenylacetophenone (DMPA; 0.4 mass % of total monomer) for 20 hours at 4° C. After removal of the tissue from the solution and removal of excess solution by blotting on tissue paper, the tissue samples were placed in a Petri dish, covered with fresh buffered saline, and exposed to long wave ultraviolet radiation (315-400 nm) for 20 minutes (10 minutes per side). Unreacted monomer was removed by 8×30 minute washes in buffered saline at 4° C. All solutions were sterilized by filtration prior to use.

In some embodiments, the monomer concentration is between 1 and 60 percent, preferably between 10 and 30 percent, by mass. The cross-linker concentration in some embodiments is between 1/10 to 1/100 that of the monomer concentration, preferably between 1/20 and 1/40 that of the monomer concentration. The initiator concentration can be from 0.01 to 5 percent, preferably from 0.1 to 1 percent, in some methods. If light sensitive initiator is used, the light exposure can be from 1-60 minutes per side, typically 10 minutes per side. The tissue can be washed with 5-20 changes within 24-72 hours, typically 5-8 times in 24 hours to remove remaining monomer.

Example 2

GA Control

Fresh, rinsed porcine tissue was cross linked by immersion in a buffered saline solution containing 0.2% glutaraldehyde (GA) at 4° C. for 7 days. This GA fixed tissue was subsequently processed according to the method outlined in Example 1.

Example 3

HEMA+bAAm

Tissue was treated according to specifications in Example 1, with the exception that 20 g/100 ml hydroxyethyl methacrylate (HEMA) was used instead of the 30 g/100 ml acrylamide. The treatment ranges described with respect to Example 1 can be used.

Example 4

Propional Block Capping of NH2

Rinsed porcine aortic tissue was incubated in 0.05M MES buffer (pH=6.4) containing 0.5M propional for 48 hours at 4° C. Sodium cyanoborohydride ($NaCNBH_3$) was added in three equal portions (at times 0, 3 and 16 hours) to obtain a final concentration of 60 mM. The tissue was subsequently washed 5 times with a 0.9 mass % sodium chloride (NaCl) solution. In general, the invention described with respect to Example 4 can be performed using MES buffer having a pH from 4 to 7, containing from 0.1 to 2M propional for from 1-96 hours at from 1 to 37 degrees C. The sodium cyanoborohydride can be added to obtain a final concentration of 10 to 300 mM. The tissue can be subsequently washed from 1 to 10 times with a 0.9 mass % sodium chloride (NaCl) solution.

Example 5

PGE Block Capping of NH2

Rinsed porcine aortic tissue was incubated in carbonate buffer containing 4 mass % glycidyl isopropyl ether (PGE) at pH=7 for 7 days and subsequently rinsed (6 exchanges of 0.9 mass % NaCl solution). The rinsed porcine aortic tissue of Example 5 can be incubated in carbonate buffer containing from 1 to 10 mass percent glycidyl isopropyl ether (PGE) at a p from 7 to 10 for between 1 and 10 days and subsequently rinsed using 6 exchanges of 0.9 mass % NaCl solution.

Example 6

PGE Block Capping of COOH

Tissue was treated according to the procedure outlined in Example 5, with the exception that the reaction was performed at pH=4.5 in order to block the tissue carboxyl groups instead of the amino groups. In some embodiments similar to that described in Example 6, the pH can be from 3 to 6.

Example 7

GMA Activation Capping

Tissue was treated according to the procedure outlined in Example 5, with the exception that Glycidyl methacrylate (GMA) was used instead of PGE in order to achieve activation capping.

Example 8

Capping, then AAm+bAAm

Porcine tissue samples prepared as per Examples 4, 5, 6 and 7 were subsequently treated according to the procedure outlined in Example 1.

Example 9

Tissue samples as prepared in Examples 1, 2, 3 and 8 (with appropriate controls) were subjected to evaluation to determine the effect of the AAm hydrogel filling on tissue properties. Mass increase, shrinkage temperature (ST), resistance to degradation by protease (RDP), Residual amine content (RAC), and tensile properties were assessed in vitro. Fibroblasts were incubated in the presence of treated tissue to show that the tissue was washed sufficiently and that no toxic monomer is released from the polymer filler.

In addition, tissue sections were prepared by standard histological techniques and stained with Haematoxylin and Eosin. FIGS. 7A and B contain photomicrographs of filled tissue (H&E stain), where FIG. 7A is fresh tissue and FIG. 7B is 0.2% GA fixed tissue (both filled with 30% Aam/bAAm). In vivo assessment of tissue calcification was performed by subcutaneous implantation in rats for 60 days. Explanted samples were analysed for calcium content by atomic absorption spectroscopy (AAS).

The staining of the acrylamide gel in the tissue allowed for the assessment of the degree to which penetration of the acrylamide monomer occurred. See FIG. 7A. It clearly showed full penetration into the fresh (unfixed) tissue (prepared as described in Example 1) (see FIG. 7A), whereas penetration of Aam into the tissue prepared according to the procedure in Example 2 was limited to the surface of the tissue (penetration limited to approximately the outer quarter of the tissue on either side). This may be seen by viewing FIG. 7B. The Aam filling of fresh tissue resulted in an increase of sample mass of about 88 percent, compared to only about 35 percent mass increase for GA pre-treated tissue.

Figure 8B:
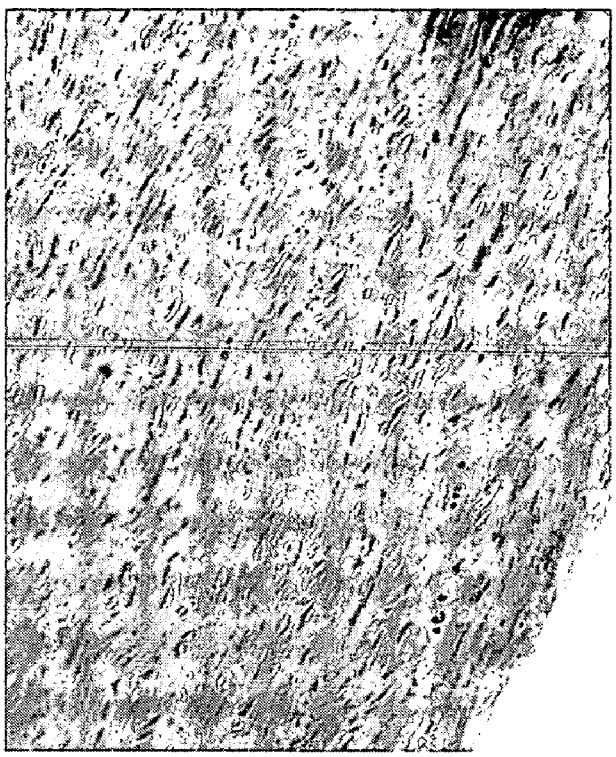
FIG. 8B is similar to FIG. 8A, but after the protease digestion, showing significant tissue structure remaining.
Figure 8A:
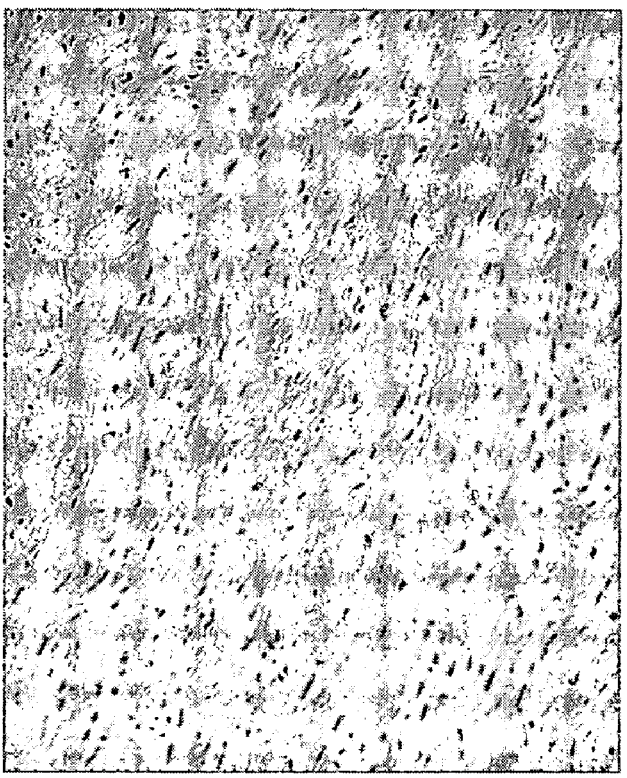
FIG. 8A is a photomicrograph of fresh tissue, not treated with GA, after in-situ polymerization with acrylamide monomer and bis-acrylamide cross-linker, before protease digestion.

FIGS. 8A and 8B contain two photomicrographs of tissue, stained with Masson's Trichrome stain. Fresh tissue was treated with 30% Aam/bAAm and then subjected to protease digestion. FIG. 8A illustrates the tissue before protease digestion while FIG. 8B shows the tissue after protease digestion. The tissue may be seen to remain intact. The resistance to degradation by protease (RDP) is summarized in the table in FIG. 10, where about 43 percent of 0.2% GA treated tissue remained, while about 30 percent of the Aam polymerized tissue remained after protease digestion.

Proposed Mechanism

Figure 9:
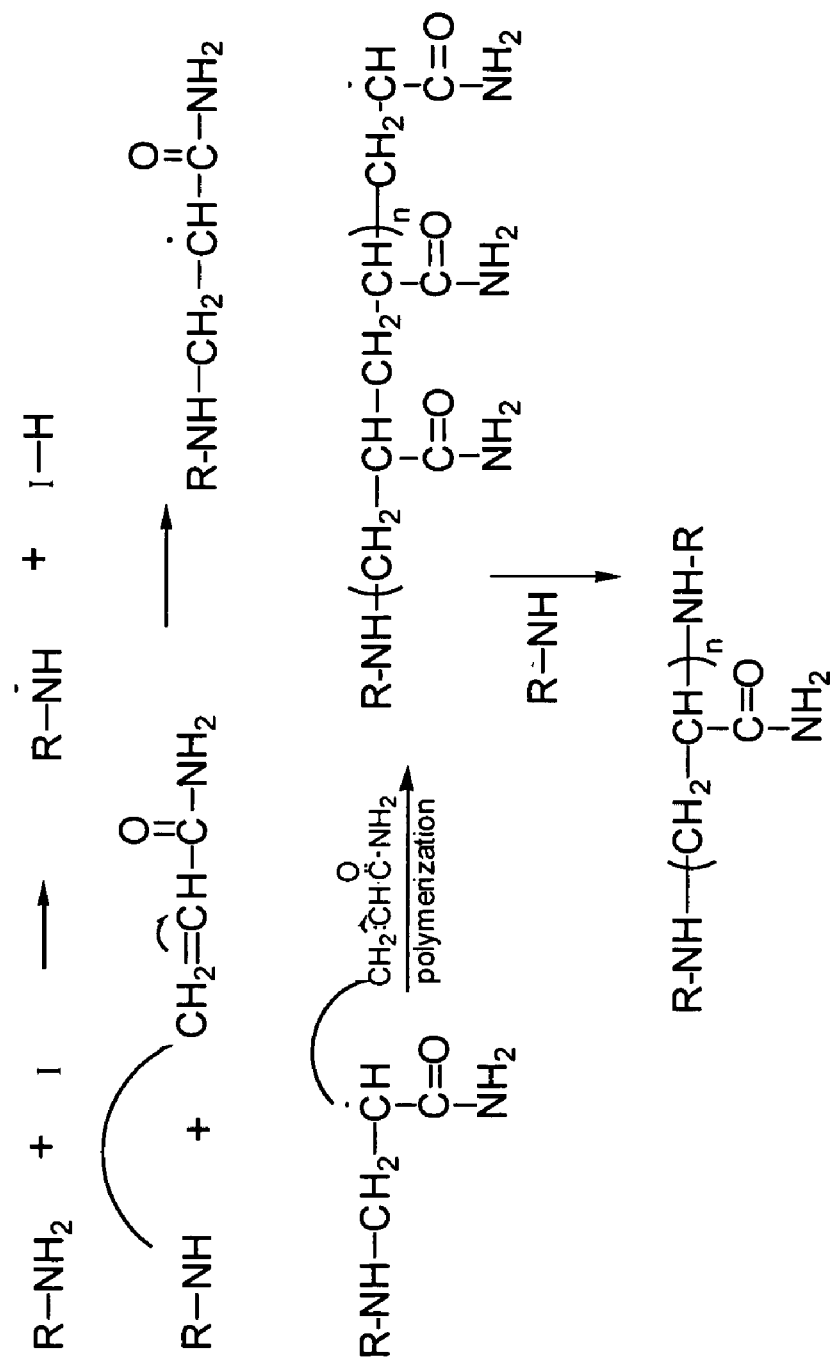
FIG. 9 includes chemical structure diagrams illustrating a proposed reaction mechanism for free radical polymerization directly to native tissue amino groups.

There is evidence (decreased amine content, increased shrinkage temperature) that the filling of tissue, e.g. according to Examples 1, 2, 3 and 8 results not only in the filling of the tissue, but also in the crosslinking of the tissue via a mechanism similar to the one shown in FIG. 9. It is noted that applicants do not wish to be bound by any particular theory, and note that certain embodiments of the present invention may provide more or less support for any particular theory.

Summary of Experimental Results

FIG. 10 is a table summarizing the experimental results from some of the examples described above. ST represents the shrinkage temperature in degrees Celsius. A higher ST is an indication of a greater degree of cross-linking. RDP represents the resistance to protease degradation. The RDP is the percent tissue remaining after degradation, based on the tissue mass only, with the hydrogel mass discounted. RAC represents the residual amine content, in units of $\mu$mol/g (micromole per gram). Stress is measured at 25 percent strain, in units of MPa. Higher stress is indicative of greater stiffness. Calcium is measured in units of $\mu$g/g (microgram per milligram).

Filling fresh (not fixed with GA) tissue with AAm (Example 1) or with HEMA (Example 3), has reduced calcification relative to 0.2% GA fixed tissue (the control), having calcification values of about 12.5 and 7 respectively, compared to about 98 for the control. The degradation resistance values for the same two examples are about 40 and 36 percent tissue remaining, compared to about 43 percent remaining for the GA fixed control. The Shrinkage Temperature (ST) values of about 73 degrees C. for Example 1 is higher than the 67 degree value for the fresh tissue, indicating that it is likely that some cross-linking has occurred. The stress values for Examples 1 and 3 are about 0.40 and 0.2 MPa, which are less than the 0.63 value for the GA control, indicating that they are less stiff than the control.

The effect of block capping fresh tissue followed by in-situ polymerization with AAm can also be seen in FIG. 10, for Example 8. The block capping decreased the shrinkage temperature relative to that of Example 1, the ST values being about 64 degrees and 73 degrees C., respectively. The block capping also reduced the RDP from about 38% for Example 1 to about 30 percent tissue remaining after protease digestion for Example 8. The stiffness was also reduced, as indicated by a stress value decreasing from about 0.40 MPa to about 0.33 MPa. The residual amine content dropped from about 100 in Example 1 to about 48 in Example 8. These results indicate that cross-linking can be decreased through block capping.

Other experimental results (not included above) indicate that when PGE is used to block either amine or carboxyl groups (at pH 10 and 4.5 respectively), or propional is used to block amine groups (at pH6.4), the tissue has a lower ST value than fresh tissue. Blocking both amine and carboxyl groups reduced the ST further. For tissue with only carboxyl groups blocked, the increase in ST after filling is significant, but not for tissue with amine groups blocked. When both amino and carboxyl groups are blocked with PGE (pH 10 and 4.5 respectively) a very significant decrease in ST is observed.

Experiments also indicate that when tissue amine groups were blocked, followed by carboxyl groups being blocked, followed by filling with 30% AAm in-situ polymerization, that 65 percent of the tissue remained after in-vitro protease digestion for 24 hours, compared to almost complete destruction of the blocked tissue without filling. Reversing the order of the capping left about 77 percent of the tissue remaining after the protease digestion. The tissue filling thus protects the tissue even after the block capping.

Figure 11B:
FIG. 11B is a photomicrograph of tissue treated with 0.2% GA (no filling), after implantation in the rat subcutaneous model and subsequent von Kossa staining, showing minimal calcific deposits, showing significant deposits of Calcium.
Figure 11A:
FIG. 11A is a photomicrograph of fresh tissue, not treated with GA, after in-situ polymerization with hydroxyethyl methacrylate monomer and bis-acrylamide cross-linker, after implantation in the rat subcutaneous model and subsequent von Kossa staining, showing minimal calcific deposits.

Combinations of different type I monomers (with inclusion of a small amount of Type II monomer to ensure 3-dimensional network of hydrogel), have been shown (results not included) to be as effective in limiting tissue calcification as either of the two Type I monomers on their own. An example of such a combination is tissue filled with 15% HEMA, 15% Aam (+bis-Aam at a ratio of 1 part bis-Aam to 36.5 parts of Aam/HEMA). Von Kossa histological stains of calcification patterns of tissue treated by this method (and evaluated in the subcutaneous model) is shown in FIG. 11A. It is clear that the level of calcification is much lower than that observed in unfilled 0.2% GA fixed tissue (FIG. 11B).

Other experimental results, not included in FIG. 10, indicate that activation capping with GMA increases the cross-link density for Aam in-situ polymerization. The results also indicate that the RDP is increased, the shrinkage temperature is increased, the residual amine content is decreased, and the tensile stress is markedly increased. These results indicate that cross-link density can be increased by activation capping.

In another experimental result, fibroblasts were incubated in the presence of treated tissue. The tissue was filled by in-situ polymerization of AAc and AAm (in different samples) and subsequently washed. The continued vitality of the fibroblasts seems to indicate that toxic monomer is not released from the polymer filler.

Prophetic Examples

Porcine aortic tissue is infiltrated with a solution containing a mixture of
   a multifunctional substrate
      2 to 8 arm polyethylene glycol functionalized with vinyl sulfone groups, and/or
      2 to 8 arm polyethylene glycol functionalized with acrylate groups A dithiol crosslinker, e.g.
3.4 kDa PEG-2SH, and/or
Dithiothreitol
(Optional) a pendant group, containing one nucleophile for attachment to the substrate.

Typically, the substrate (e.g. n-arm PEG-VS) is reacted with the optional pendant group(s) in a buffered solution. The pendant group(s) is (are) added in ratios low enough as not to prevent subsequent crosslinking of the substrate with the crosslinker. The crosslinker is subsequently added to the pendant-group-derivatized substrate. The resultant reaction mixture is then infiltrated into the tissue. Vacuum and/or pressure may be used to increase the rate of penetration. The infiltration conditions, e.g. pH and temperature profiles are controlled in such a way as to allow optimal penetration of the reaction mixture before gellation occurs, and also such that full gellation of the reaction mixture is eventually achieved (after infiltration).

GA Fixation After In-Situ Polymerization

In another aspect of the invention, in a prophetic example, GA or other cross-linking can be performed after in-situ polymerization. Tissue can be treated according to examples 1, 3, 4, 5, 6, 7, 8, or the prophetic example(s) above, and then cross-linked with GA, for example that of example 2, or similar or alternate cross-linking.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

The invention claimed is:

1. A method for in vitro treatment of bioprosthetic-tissue for implantation into a human body, the method comprising:
providing bioprosthetic-tissue comprising amino groups and carboxyl groups;
providing a first compound having at least one vinyl moiety;
introducing the first compound into interstitial spaces of the tissue; and
polymerizing the first compound with a free radical initiator in the interstitial spaces of the tissue to form a hydrogel polymer,
wherein the vinyl moiety reacts with at least some of the amino groups to bind at least some of the hydrogel polymer to the tissue amino groups; and essentially none of the tissue amino groups are cross-linked with glutaraldehyde;
whereby calcification in the bioprosthetic tissue is reduced post implantation.

2. The method of claim 1, wherein the free radical initiator is selected from the group consisting of thermal initiators, peroxy compounds, azo compounds, photo initiators, redox initiators, and radiation induced initiators.

3. The method of claim 1, further comprising contacting a second compound that is different from the first compound to the tissue, and wherein the reacting includes cross-linking the second compound to the polymer.

4. The method of claim 3, wherein the second compound has at least two vinyl moieties.

5. The method of claim 4, wherein the second compound comprises PEG.

6. The method of claim 5, wherein the second compound comprises PEG in a compound backbone.

7. The method of claim 5, wherein the second compound comprises PEG in a compound sidearm.

8. The method of claim 3, wherein the second compound is selected from the group N,N'-methylenebisacrylamide, N,N'-(1,2-dihydroxyethylene)-bisacrylamide, polyethyleneglycol divinyl ether, and

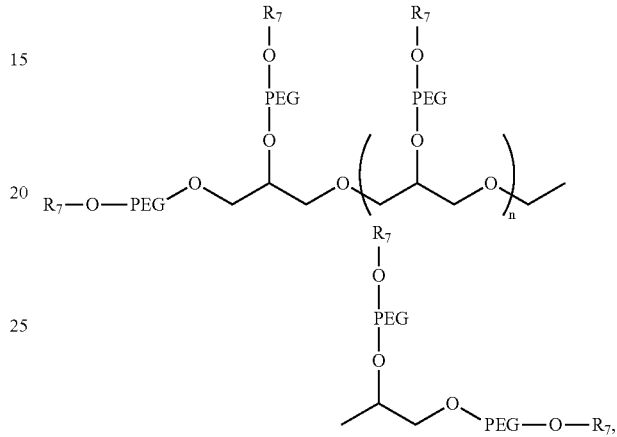

where $R_7$ contains a vinyl group and n is an integer 1 or greater.

9. The method of 1, wherein the first compound has the formula $R_1R_2C{=}CR_3R_4$, wherein each of $R_1$, $R_2$, and $R_3$ is H or $CH_3$, and wherein $R_4$ is selected from the group alkyl, aryl, ether, acid, ester, amide, alcohol and amine.

10. The method of claim 9, wherein $R_4$ is selected from the group —COOH, —COOR$_5$, —CONH$_2$, and —CONHR$_6$, wherein $R_5$ is an alcohol, and wherein $R_6$ is an alkyl.

11. The method of claim 9, wherein $R_4$ is selected from the group —COOH, —COOR$_5$, —CONH$_2$, and —CONHR$_6$, wherein $R_5$ has the formula —(—CH$_2$—)$_n$—OH and n=1 or greater, and wherein $R_6$ has the formula —(—CH$_2$—)$_p$—CH$_3$ and p is 0 or greater.

12. The method of 1, wherein the first compound is selected from the group acrylamide, 2-hydroxy ethyl methacrylate, methyl crotonate, methyl acrylate, ethyl acrylate, N(hydroxymethyl) methacrylamide, methyl methacrylate, methacrylamide, and N(hydroxymethyl) acrylamide and any combinations thereof.

13. The method of claim 12, wherein the first compound is acrylamide.

14. The method of 1, wherein the first compound has at least two vinyl moieties.

15. The method of claim 14, wherein the first compound comprises PEG.

16. The method of claim 15, wherein the first compound comprises PEG in a compound backbone.

17. The method of claim 15, wherein the first compound comprises PEG in a compound sidearm.

18. The method of claim 1, further comprising capping at least some of the amino groups with a block capping agent.

19. The method of claim 18, wherein the capping provides non-reactive groups selected from the group alkyl, aryl, ether and alcohol groups.

20. The method of claim 18, wherein the block capping agent is selected from the group glycidyl ether (PGE), glyceral, propional, $CHO(CH_2)_nCH_3$, and $CH_3CO(CH_2)_nCH_3$, where n is an integer having a value or 0 or greater, and any combination thereof.

21. The method of claim 1, further comprising capping at least some of the carboxyl groups with a capping agent.

22. The method of claim 21, wherein the capping provides non-reactive groups selected from the group alkyl, aryl, ether and alcohol groups.

23. The method of 1, further comprising capping at least some of the amino groups with an activation capping agent to provide essentially reactive groups covalently bonded to the amino groups.

24. The method of claim 23, wherein the activation capping agent is selected from the group allyl glycidyl ether, butadiene monoxide, 1,2-epoxy-5-hexene, and glycidyl methacrylate, and any combination thereof.

25. The method of 1, wherein the tissue is porcine tissue.

* * * * *